United States Patent [19]

Galline et al.

[11] Patent Number: 4,889,110

[45] Date of Patent: Dec. 26, 1989

[54] ATTACHING DEVICE AND TOOLS FOR POSITIONING SAME, ESPECIALLY FOR ATTACHING THE TROCHANTER MAJOR TO THE FEMUR

[76] Inventors: Yves Galline, 4 route d'Aigremont, 78240 Chambourcy; Claude Soria, 3 rue de la Forêt, La Trigale, les Ventes, 27180 St Sebastien de Morsent, both of France

[21] Appl. No.: 187,085

[22] Filed: Apr. 28, 1988

[30] Foreign Application Priority Data

May 5, 1987 [FR] France .................. 87 06293

[51] Int. Cl.$^4$ ............................. A61G 5/04
[52] U.S. Cl. ............................. 606/69; 140/121; 254/199; 403/193; 403/389; 403/396; 606/72; 606/96
[58] Field of Search ............... 403/389, 396, 122, 234, 403/237, 192, 193, 194, 197, 199, 201, 280–282; 248/49, 63; 623/16, 22, 23; 128/92 Z, 92 ZZ, 92 ZY, 92 Y, 92 YP, 92 YL, 92 YJ, 92 YF, 92 YD, 92 V, 92 VV, 92 VD, 92 VK, 334 R, 92 R, 303 R; 24/17 A, 17 B, 115 H, 132 WL, 172, 173, 182; 29/282; 140/93.2, 93.4, 121; 100/29, 30, 32; 254/199; 73/862.39, 862.42

[56] References Cited

U.S. PATENT DOCUMENTS

| | | | |
|---|---|---|---|
| 2,267,532 | 12/1941 | Moberg | 100/30 X |
| 2,455,609 | 12/1948 | Scheib | 140/121 X |
| 2,670,015 | 2/1954 | Reynolds | 140/121 |
| 3,791,210 | 2/1974 | Taylor | 73/862.39 |
| 4,217,665 | 8/1980 | Bex et al. | 128/334 R X |
| 4,269,180 | 5/1981 | Dall et al. | 128/92 YP |
| 4,587,963 | 5/1986 | Leibinger et al. | 128/92 YD |
| 4,738,155 | 4/1988 | Stocker | 403/197 X |

FOREIGN PATENT DOCUMENTS 3146634  3/1986  Fed. Rep. of Germany ........ 128/92 YD Primary Examiner—Richard J. Apley
Assistant Examiner—David J. Bender
Attorney, Agent, or Firm—Bell, Seltzer, Park & Gibson

[57] ABSTRACT

An attaching device includes an anchoring plate 11 having four bores 12, 13, 14, 15 receiving two crimping tubes 19, 29 and two crimping rings 17, 18 for holding a multi-ply cable 20 or 21. The crimping tubes are adapted to be placed into holes drilled through the femur below the trochanter major, so as to guide the cables 20, 21 passing through the femur wall. The device is adapted to be used for attaching the trochanter major to the femur in the case of a trochanterotomy.

14 Claims, 2 Drawing Sheets

ATTACHING DEVICE AND TOOLS FOR POSITIONING SAME, ESPECIALLY FOR ATTACHING THE TROCHANTER MAJOR TO THE FEMUR

FIELD OF THE INVENTION

The present invention relates, on the one hand, to an attaching device especially adapted to be used for attaching the trochanter major to the femur and, on the other hand, to tools for positioning such device.

BACKGROUND OF THE INVENTION

According to known methods the articulation of the hip is replaced by two prostheses, to with, a prosthesis of the neck of the femur and a prosthesis of the acetabulum of the hip-bone. One of the methods used for positioning such prostheses is the trochanterotomy which consists in cutting the trochanter major to which the ligaments of the mean gluteal muscles (gluteus medius) are attached, whereby the medullary canal or duct becomes more easily accessible, the tail portion of the femur neck prosthesis being then introduced into said duct and cemented therein. The trochanter major is then reintroduced onto the femur and fixed in this position by various means the nature of which depends on the surgeons carrying out the operation.

Amongst said various means, reference may be made, in the first place, to a one-ply wire used to surround the trochanter major so to press it against the femur. Such an attachment means is difficult to use since it fails to conform easily to the bone; also, it requires a fixation obtained by twisting and, furthermore, it irritates the muscular masses.

Other surgeons use screwed-on plates, hooks and clamps either separately or in combination with metallic encircling components; however these attachments are bulky and difficult to position in the desired site. In fact these metallic elements are too rigid to be suitable for use unless they are specially adapted to the conditions of each particular case. Furthermore their implantation at the level of the gluteus medius tendon is difficult and uncertain on account of the muscular contractions.

The one-ply wire used in most cases can be replaced by a multi-ply cable which exhibits greater flexibility and mechanical resistance and is easier to handle than the one-ply (or single-strand) wire, but is more difficult to fix since it requires the use of a plate disposed at the level of the gluteus medius tendon.

In addition to the above outlined drawbacks all the known means mentioned herein-before are unsatisfactory in that they fail to exhibit, on account of their position, a required maximum strength with respect to the tractive forces of the muscles attached to the trochanter major, since they are meant essentially to apply the trochanter major against the longitudinal portion of the femur while maintaining a transverse pressure, whereas the tractive forces of the muscles are exerted mainly in the longitudinal direction.

It is one object of the present invention to provide an attaching device, especially for attaching the trochanter major to the femur, which confers on the trochanter major a greater resistance to the tractive forces of the muscles that are attached thereto.

It is also an object of the present invention to provide an attaching device comprising multi-ply cable means and simple multi-ply cable fixing means which are not undesirably bulky.

It is a further object of the invention to provide tools for positioning the attaching device according to the invention in a desired site.

SUMMARY OF THE INVENTION

With these and other objects in view, the invention provides an attaching device especially for attaching the trochanter major to the femur, which comprises an anchoring plate that supports at least one crimping tube for at least one multi-ply tractive cable and at least one crimping ring for said cable. Said plate is anchored in the femur through at least one hole provided beneath the trochanter major and receiving the crimping tube, the free end of said multi-ply cable being threaded and crimped into said crimping ring located on the outer side of the femur when the cable has been passed through the interior of the femur and around the trochanter major so as to issue from the end of the latter and when said cable has been tightly fitted onto the trochanter major.

Preferably said anchoring plate is provided with at least two bores one of which is adapted to receive said crimping tube, while the other one of said bores is adapted to receive said crimping ring.

The respective directions, with reference to the longitudinal axis, of the crimping tube and the crimping ring form between them a certain angle under conditions that will be described herein-after, such angle being comprised between 30° and 60°, preferably between 35° and 42°.

According to another embodiment of the invention each crimping tube has at its end opposite to the cable an enlargened portion engaging the anchoring plate, and each crimping ring has at its end opposite to the cable an enlargened portion engaging the anchoring plate, said enlargened ring portion being provided with a passage for the cable.

The present invention also provides a tool for positioning the attaching device according to the invention in a desired site, which tool comprises a positioning and guiding plate that supports only the crimping rings, whereas the crimping tubes are replaced by bores for positioning the tubes and for defining a passage for multi-ply cables to be introduced into the femur below the trochanter major; the surface of the plate which faces the femur is provided with positioning lugs for angularly positioning said tool.

The present invention furthermore provides a tool for tightening each multi-ply cable once the latter has been passed into the femur, around the trochanter major and through the crimping ring, said tool comprising a retractor or forceps having two pivotable arms of respective levers arranged in a pliers-like manner and which are adapted to be angularly spaced from each other by means of a handle constituted by the two remaining arms of said levers, said two levers being pivotally connected to each other in the zone located between said arms in the shape of pliers and the arms forming said handle; each end of the part in the shape of pliers is provided with a transverse bore or orifice for the passage of said multi-ply cable, and the orifice of one of said arms in the shape of pliers is provided with a cable holding or stop screw, while the branches of the retractor comprise a return-spring which normally maintains the pliers in the closed position, and a toothed rack which maintains the pliers in a mutually spaced position for providing the desired tension of the cable while the latter is being tightened.

One of the arms in the shape of pliers comprises a dynamometer adapted to measure the value of the tensile force exerted on the cable at the time of crimping the same in the crimping rings.

One of the ends of said rack is pivotally mounted on one of said arms, while the free other end thereof is introduced into a slot provided in the other arm, said rack having catching or stop teeth which cooperate with a lug for maintaining the arms in their mutually spaced position when said cable has been tightened. The spacing spring is provided with a slot in which the rack is slidingly engaged.

BRIEF DESCRIPTION OF THE DRAWINGS

These and other features and advantages of the attaching device and the tools for positioning thereof in accordance with the present invention will be more clearly apparent from the following description which is given by way of illustration, but not of limitation, and which refers to the appended drawing.

In the drawings.

DETAILED DESCRIPTION OF THE PREFERRED EMBODIMENT

Figure 1:
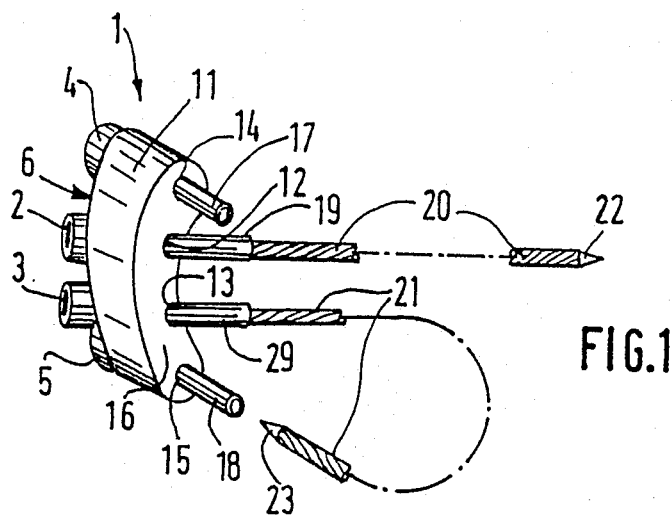
FIG. 1 is a perspective view of an attaching device according to the present invention, which is adapted to be applied to the trochanter major of a femur.

As shown in FIG. 1, the attaching device 1 according to the invention comprises a plate 11 having a comparatively great, thickness and provided with four bores 12, 13, 14 and 15. The plate 11 constitutes an anchoring plate for the cables and is pre-shaped according to a curved profile so as to be conveniently adaptable to the outer surface of the femur. Bores 14 and 15 are drilled so as to start from a lateral planar surface 16 of plate 11 and comprise two crimping rings 17 and 18. Bores 12 and 13 are drilled as explained in more detail hereinbelow according to a certain angle, with respect to the direction perpendicular to planar surface 16, and are provided with crimping tubes 19, 29 that are in fact similar to the crimping rings 17 and 18 and wherein are fixed two multi-ply cables 20 and 21 which are thus integrally connected to plate 11. The crimping rings 17 and 18 and the crimping tubes 19 and 29 introduced respectively into bores 14, 15, 12, 13 are terminated each by a respective portion 4, 5, 2, 3 having an enlargened diameter so as to prevent rings 17, 18 and tubes 19, 29 from being extracted from plate 11 in the direction opposed to said enlargened portions, whereby a traction force can be exerted on plate 11 in said direction. Portions 4 and 5 corresponding to rings 17 and 18 are provides with bores so as to allow the cables to pass there through. The rings and the cables are preferably fixed in the bores by any convenient means with a view to preventing them from being extracted in the opposite direction, i.e. on the side of the enlargened portions. It will also, be seen that on account of the angle formed between rings 17, 18 and tubes 19, 29, the enlargened portions 4, 5, 2, 3 rest on surfaces having different shapes, portions 2 and 3 resting on a bevelled portion, while portions 4 and 5 rest on a portion having a straight section.

Figure 6:
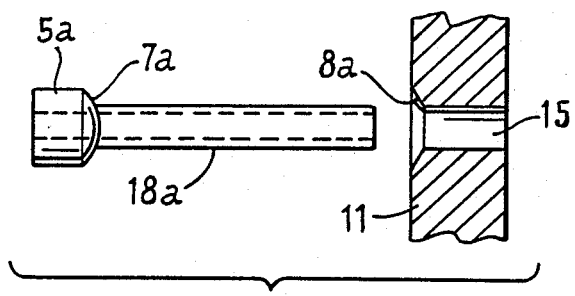
FIG. 6 is an enlarged fragmentary cross section veiw illustrating an alternative embodiment of the crimping rings and bores.
Figure 7:
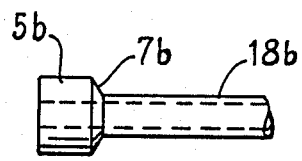
FIG. 7 is an enlarged fragmentary view similar to FIG. 6 illustrating a further alternative embodiment of the crimping rings.

According to an embodiment preventing the multiply cables 20 and 21 from being ruptured due to the alternating flectional loads exerted on them when mounted onto the prosthesis carried by the patient, crimping rings 17, 18 and crimping tubes 19, 29 may be anchored on a conical supporting surface 8a (FIG. 6), or preferably on a spherical supporting surface provided at the outlet of bores 12, 13, 14, 15 on the side of said enlargened portions 2, 3, 4, 5. The crimping rings and tubes are then terminated on the enlargened side by a head portion having a spherical supporting surface such as illustrated in FIG. 6 engages the supporting surface provided at the outlet of the bores while being enabled by their supporting surface to be displaced according to a certain rotational angle within said bores 12, 13, 14, 15. For this purpose the orifices of said bores may form a bore having a diameter greater than that of ring 17, 18 or tube 19, 29, or a bore having a slightly conical shape flaring in the direction of cable 20 or 21. In a further alternative embodiment, the enlarged head portions 5b may have a conical supporting surface 7b such as illustrated in FIG. 7.

Multi-ply cables 20 and 21 have a length sufficient to allow them to be handled easily when being positioned in the desired site, and their ends are provided with welded points 22 and 23. As will be explained in more detail with reference to the following figures, said ends 22 and 23 are adapted to be introduced into the crimping rings 17 and 18. The other ends are introduced into the tubes 19 and 29 where they are crimped by any convenient means, such as —especially—by pinching.

Figure 5:
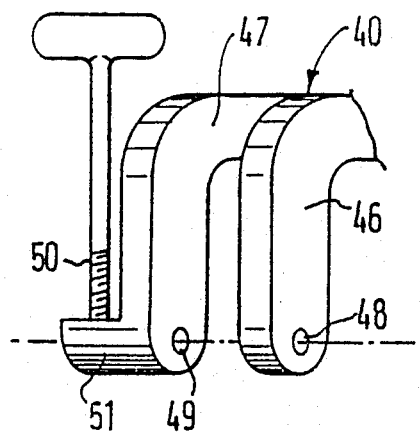
FIG. 5 is a perspective view of the tool constituting pliers, which is used for tightening the multi-ply cable.
Figure 4:
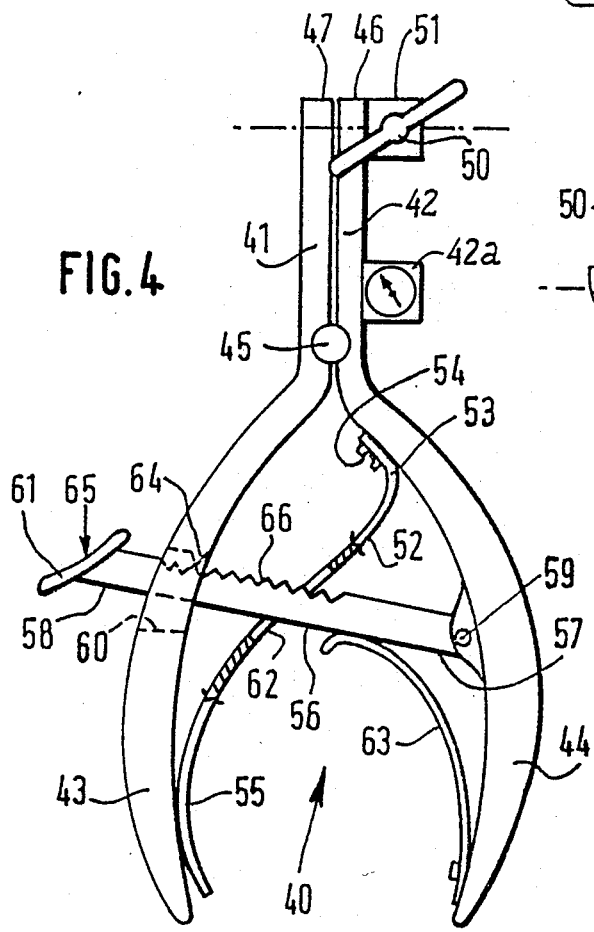
FIG. 4 is a lateral view of the tool for tightening the multi-ply cable.

By means of a tool according to the invention, which will be described herein-after with reference to FIGS. 4 and 5, the surgeon tightens cables 20 and 21 under a convenient tractive force, introduces said cables into rings 17 and 18 and then cuts the protruding portions flush with the outlet orifice of the crimping rings.

Figure 3:
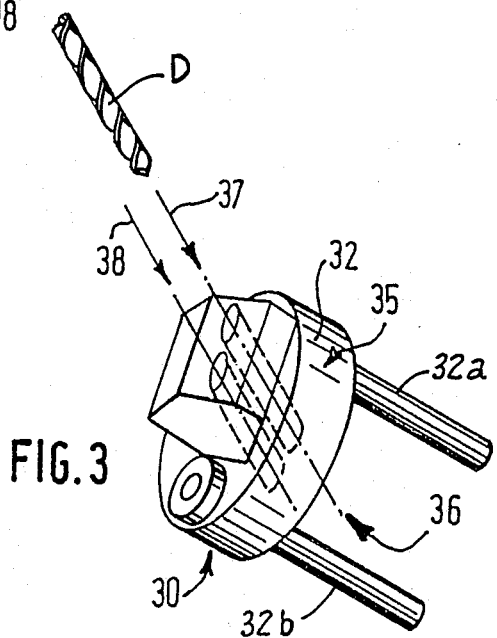
FIG. 3 is a lateral view of the positioning tool for producing the passage holes of the multi-ply cables in the femur.

For facilitating the operation of drilling holes in the femur for introducing crimping tubes 19 and 29 as well as cables 20 and 21 therein, a tool 30 as shown in FIG. 3 may be used; which tool constitutes, in fact, a calibrating or "phantom" tool for positioning and guiding purposes. It comprises a plate 32 similar to plate 11 (FIG. 1), as far as the size is concerned, and crimping rings; however it is different from plate 11 in that the crimping tubes and the cables are omitted, so as to expose orifices 37 and 38. Furthermore, positioning lugs 32a and 32b may be provided on the plate inner side 36 which is generally concave. In this case, the lugs 32a and 32b are preferably provided on the inner face 36 of plate 32, which side is adapted to be applied against the femur. Orifices 37 and 38 constitute the inlets of guiding channels provided in plate 32 and arranged in a manner similar to that of the crimping tubes according to a direction that is not parallel to that of the crimping rings, said two directions thus being angularly shifted with respect to each other.

Holes are drilled by drill D into the femur in front of orifices 37 and 38 and during the tightening of the cables, as described herein-after, tubes 19 and 29 which are held in said holes prevent plate 32 from sliding on the surface of the femur. Indeed the muscular tractive forces exerted on one trochanter major while the subject (or patient) raises the other leg may be higher than 200 daN for an average adult person. It is thus required that the angle at which the tubes are implanted into the bone be correctly selected so that, on the one hand, the fixing is sufficiently strong to resist such tractive forces and, on the other hand, the tubes as positioned show no tendency to be extracted. The angle formed by the longitudinal axis of a ring 17, 18 and the longitudinal axis of the corresponding tubes 19, 29 is advantageously comprised between 30 and 60°, preferably between 35 and 42°.

The guiding tool constituted by plate 32 is used by the surgeon on the one hand with a view to facilitating the positioning of the holes for passing the cables through the femur by applying the crimping rings (and possibly the lugs, not shown in the drawing) onto the femur and, on the other hand, with a view to facilitating the operation of drilling the holes for passing the cables through the femur, using a drill which is guided by the passages defined by the crimping tubes.

The multi-ply cable tightening tool will be described herein-below with reference to FIGS. 4 and 5. Said tool 40 is constituted by an extractor or forceps having two levers pivotally mounted onto each other at a fulcrum point 45, said levers comprising arms 41 and 42 that form pliers, as well as actuating arms 43 and 44 forming a handle. Each one of the arms in the shape of pliers is extended by a curved portion 46 and 47 (FIG. 5) located in a plane perpendicular to that of FIG. 4. The end of each curved portion is provided with a transverse bore 48 and 49, respectively into which a multi-ply cable can be introduced. Bores 48 and 49 are substantially aligned with respect to each other. Bore 48 constitutes a free passage, whereas bore 49 is associated to a stop screw 50 mounted on a block 51 that extends bore 49 towards the outer side of pliers 42. Block 51 may be equipped with a dynamometer 42a (of the spring type, for example) that allows one to measure the value of the tractive force exerted on the multi-ply cable during handling of the pliers, especially with a view to balancing the tractive forces exerted on the two cables 20, 21 cooperating with plate 32.

In the rest position the arms forming the pliers 41, 42 are maintained in engagement with each other by a return spring 52 mounted between arms 43 and 44, one end 53 of said spring being attached to the inner side of arm 44 by screws 54, while the other end 55 of the spring is movable and is pressed against the inner side of arm 43.

A toothed rack 56 is disposed between arms 43 and 44 so as to be able to slide, with a certain play or clearance in a slot 60 of arm 43 and a slot 62 of return-spring 52. One end 57 of rack 56 is hingedly mounted on an axis 59 supported by arm 43, while the other end 58 is free and is provided with a rack-releasing pushing element 61. The rack is provided with teeth 66 cooperating with at least one lug 64 provided in slot 60 in such a manner that, depending on the angular distance between arms 43 and 44, or between arms 41 and 42 in the shape of pliers, one given tooth of the rack engages lug 64. In order to ensure such engagement, a spring 63 is mounted on arm 44 and adapted to bias the rack upwardly. Disengagement from lug 64 is obtained by manually applying a force onto pushing element 61 in the direction of arrow 65.

Figure 2:
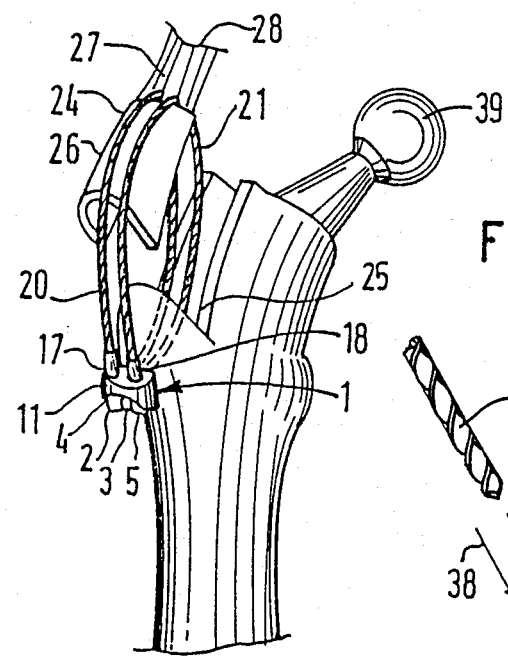
FIG. 2 is a perspective view of the attaching device and the end of a femur, the trochanter major being detached from its notch, while the prosthesis of the femur head is positioned in the desired site.

The attaching device 1 on a femur is positioned as described herein-below and illustrated in FIG. 2. One the trochanter major 24 has been severed by sawing, while yet still being connected to the muscle by tendons 28, tool 32 of FIG. 3 is placed in a position substantially perpendicular to the bone at a location selected for positioning plate 11. Crimping rings 17 and 18 are disposed along the surface of the bone and oriented upwardly. The femur is drilled below the trochanter major by means of a drill guided by bores 37 and 38.

Using any convenient known means, cables 20, 21 are introduced into the holes thus drilled in the femur, said cables passing from the outside toward the inside, and then being pulled upwardly into the medular duct, while positioning plate 11 by inserting tubes 19, 29 into the holes or bores previously drilled in the femur.

Cables 20, 21 are then passed around the trochanter major at 24 through the ligamentary base of tendons 28 so as to apply them onto the outer surface of the trochanter which is re-positioned on the femur. Then cable 20, 21 are passed through rings 17, 18 and pulled so as to firmly position the trochanter major on the femur, a controlled tractive force being exerted for this purpose on the cable, possibly through the intermediary of the dynamometer mounted on the end (e.g. block 51) of the retracting tool 40.

Retractor or forceps 40 is then used as follows. Once cable 21 has been introduced through crimping ring 18, for example, said cable is introduced into, and passed through, bore 48 of arm 41 of the pliers, then into bore 49 of arm 42 of said pliers. The closed pliers are then displaced toward plate 11 so that lever arm 41 exerts a pressure on the plate. In this position the surgeon blocks the cable by means of stop screw 50 and then manually acts, by one hand, on arms 43 and 44 so as to close the same and thus open the lever arms 31 and 42 in the shape of pliers; thereby cable 21 is pulled and submitted to a tractive or tightening force of a predetermined value (possible under the control of the dynamometer mounted on block 51). This tension is maintained by the engagement of the successive teeth of the rack with lug 64 under the action of spring 63. Due to this mainting effect the surgeon's hand is freed, so that he can now proceed with an other operation such as tightening the other cable 20 by means of a second retractor or forceps arranged symmetrically with respect to the first one. It is thus possible to tighten progressively the retractors so as to avoid any lack of symmetry as regards the tightening said cables by a desired tractive force. Furthermore, such tightening operation ensures perfect positioning of plate 11 the tubes 19, 29 of which penetrate deeply and entirely the holes or bores drilled in the femur. When the tractive forces (or tightening forces) are sufficient for satisfactorily maintaining the trochanter major in the desired position, rings 17, 18 are crimped onto cables 20, 21; thereafter the retractors are removed and the cables are severed flush with the crimping ring, by means of a convenient tool.

The attaching device and certains tools for positioning such device have been described herein-above with reference to attaching the trochanter major to the femur; it is obvious, however, that they may be used in other applications without departing from the scope of the present invention. Variants and/or modifications can also be envisaged, particularly as regards the respective positions of the crimping tubes and the crimping rings.

It will be noted that during the tightening operation the enlargened portions 2, 3, 4, 5 of rings 17, 18 and tubes 19, 29 rest on plate 11 and are subjected to the tractive forces of the cables to which are added the tractive forces that the muscles exert on the trochanter major, and that, consequently, said portions should be able to withstand forces as high as several daN.

It will also be noted that the embodiment shown in the figures two cables are provided which pass through two tubes and two rings (such arrangement being preferred with a view to balance the forces acting on the trochanter major). This construction is not necessary, in all cases, as far as the arrangement of the rings is concerned, and it may be modified so as to adapted to other application which do not involve the trochanter major. It is also obvious that, without departing from the spirit of the invention, any number of cables may be provided, or even one single cable, depending on the envisage application, especially in fields other than surgery.

To resume, it should be well understood that the present invention is not limited to the embodiments described and shown herein, many variants and modifications may be envisaged by those skilled in the art without departing from the spirit and scope of the invention as defined in the appended claims.

We claim

1. An attaching device especially suited for attaching the trochanter major to the femur comprising an anchoring plate having at least two bores extending through said anchoring plate, at least one crimping tube carried by said anchoring plate and positioned in one of said bores, at least one crimping ring carried by said anchoring plate and positioned in a second of said bores, and at least one multi-ply tractive cable having one end crimped in said at least one crimping tube and its other end adapted to be received in and through said at least one crimping ring.

2. A device according to claim 1, wherein said anchoring plate supports two crimping tubes and two crimping rings for two multi-ply cables, and wherein said two crimping tubes are located between said crimping rings.

3. The attaching device according to claim 1, wherein each crimping tube has an elongated end portion at an end opposite the end receiving the cable and wherein the enlarged end portion rests on said anchoring plate.

4. The device according to claim 3, wherein said enlarged end portion has a spherical shape.

5. The device according to claim 1, wherein each crimping ring has an enlarged end portion at an end opposite the end which receives the cable, and wherein said enlarged portion rests on said anchoring plate and is provided with a passage for said cable.

6. The device according to claim 5, wherein said enlarged end portion has a conical or sperical shape.

7. A kit including an attaching device as defined in claim 1, and a retractor tool for tightening said multi-ply cable when attaching the trochanter major to the femur, said retractor tool comprising two levers pivotally connected to each other, each lever including a first arm forming a plier tong and a second arm forming a handle, and wherein each said first arm includes a bore forming a passage for the cable, one of said first arms being provided with a stop screw for the cable, and wherein said second arms are provided with an opening spring and a rack adapted to maintain mutual spacing of said second arms.

8. The kit according to claim 7, wherein said rack is pivotally mounted on one of said second arms, and wherein the other of said second arms includes a slot with a lug to receive the other end of said rack, and wherein said rack is provided with catching teeth cooperating with said lug for maintaining the mutual spacing of said arms.

9. The kit according to claim 7, wherein said opening spring on said retractor tool is provided with a slot in which said rack is slidably mounted.

10. An attaching device especially suited for attaching the trochanter major to the femur comprising an anchoring plate, at least one crimping tube carried by said anchoring plate, at least one crimping ring carried by said anchoring plate, at least one multi-ply tractive cable having one end crimped in said at least one crimping tube and its other end adapted to be received in said at least one crimping ring, wherein said anchoring plate includes at least two bores, one of which receives said at least one crimping tube, and the other bore receiving said at least one crimping ring, and wherein said bore which receives said crimping ring has a diameter greater than that of said crimping ring.

11. An attaching device especially suited for attaching the trochanter major to the femur comprising an anchoring plate, at least one crimping tube carried by said anchoring plate, at least one crimping ring carried by said anchoring plate, and at least one multi-ply tractive cable having one end crimped in said at least one crimping tube and its other end adapted to be received in said at least one crimping ring, wherein the longitudinal axis of said at least one crimping tube is oriented with respect to the longitudinal axis of said at least one crimping ring to form an angle of between 30 and 60 degrees.

12. The device according to claim 11, wherein said angle is between 35 and 42 degrees.

13. A kit including an attaching device especially suited for attaching the trochanter major to the femur comprising an anchoring plate, two crimping rings carried by said anchoring plate, two crimping tubes carried by said anchoring plate between said crimping rings, and two multi-ply tractive cables each having one end crimped in one of said crimping tubes and its other end adapted to be received in one of said crimping rings, a tool for positioning said attaching device in a desired site on the femur below the trochanter major, said tool comprising a positioning and guiding plate having a lower surface adapted to be positioned facing the femur, said guiding plate supporting said crimping rings, and said guiding plate including bores for guiding a drill.

14. The kit as defined in claim 13, wherein the lower surface of said positioning and guiding plate includes positioning lugs.

* * * * *